United States Patent [19]

Baker et al.

[11] Patent Number: 4,839,174
[45] Date of Patent: Jun. 13, 1989

[54] NOVEL TRANSDERMAL NICOTINE PATCH

[75] Inventors: Richard W. Baker, Palo Alto; Frank Kochinke, Mt. View; Carl Huang, Palo Alto, all of Calif.

[73] Assignee: Pharmetrix Corporation, Menlo Park, Calif.

[21] Appl. No.: 105,549

[22] Filed: Oct. 5, 1987

[51] Int. Cl.$^4$ .......................... A61L 15/00; A61B 5/00
[52] U.S. Cl. .................... 424/447; 424/448; 424/486; 424/449; 131/335; 128/156; 128/632
[58] Field of Search ............... 131/335; 128/632, 156; 424/449, 447, 448, 486

[56] References Cited

U.S. PATENT DOCUMENTS

| 3,598,122 | 8/1971 | Zaffaroni | 128/268 |
|---|---|---|---|
| 3,598,123 | 8/1971 | Zaffaroni | 128/268 |
| 3,731,683 | 5/1973 | Zaffaroni | 128/268 |
| 3,742,951 | 7/1973 | Zaffaroni | 128/268 |
| 3,797,494 | 3/1974 | Zaffaroni | 128/268 |
| 3,996,934 | 12/1976 | Zaffaroni | 128/268 |
| 4,597,961 | 7/1986 | Etscorn | 424/449 |
| 4,624,665 | 11/1986 | Nuwayser | 424/448 |
| 4,627,429 | 12/1986 | Tsuk | 424/449 |
| 4,638,043 | 1/1987 | Szycher et al. | 424/449 |
| 4,687,481 | 8/1987 | Nowayser | 424/449 |
| 4,706,676 | 11/1987 | Peck | 128/632 |
| 4,715,387 | 12/1987 | Rose | 131/335 |

FOREIGN PATENT DOCUMENTS

| 3438284 | 7/1985 | Fed. Rep. of Germany . |
| 0084817 | 5/1984 | Japan . |
| 61-251619 | 8/1986 | Japan . |
| 8702870 | 5/1987 | World Int. Prop. O. . |
| 8801497 | 3/1988 | World Int. Prop. O. . |

OTHER PUBLICATIONS

J. E. Rose et al., "Transdermal Administration of Nicotine", *Drug and Alcohol Dep.*, 13, 209-213, 1984.
J. F. Komerska, "Urethane Films—Transdermal Opportunities", *J. Plastic Film and Sheeting*, 3, 58-64, 1987.

*Primary Examiner*—Ellis P. Robinson
*Assistant Examiner*—P. J. Ryan
*Attorney, Agent, or Firm*—J. Farrant

[57] ABSTRACT

A controlled release transdermal delivery system for nicotine administration. The system comprises an impermeable backing layer, a polyurethane matrix layer containing between about 5 wt % and 50 wt % nicotine, and an adhesive skin-contacting layer. The system is designed to administer nicotine for smoking cessation therapy or other uses over a period of 24 hours or more.

7 Claims, 2 Drawing Sheets

NOVEL TRANSDERMAL NICOTINE PATCH

This invention was made with Government support under Grant Number R43 DA 04249 awarded by the DHSS, Alcohol, Drug Abuse and Mental Health Administration. The Government has certain rights in this invention.

FIELD OF THE INVENTION

The invention relates to a controlled release transdermal delivery system for administering nicotine.

BACKGROUND OF THE INVENTION

Delivery of drugs by the transdermal route has been known to be theoretically possible for many years. The earliest patented transdermal devices were medicated bandages, usually with the drug mixed into the adhesive, that were designed to bring a known quantity of drug to a known area of skin for a known time. Such devices usually did not control the rate at which the drug was released. Since the 1970's interest in using the transdermal route for controlled release therapy has grown substantially, as evidenced by the large number of U.S. Patents in the area now. Controlled release transdermal devices rely for their effect on delivery of a known flux of drug to the skin for a prolonged period of time, generally a day, several days, or a week. Two mechanisms are used to regulate the drug flux: either the drug is contained within a drug reservoir, which is separated from the skin of the wearer by a synthetic membrane, through which the drug diffuses; or the drug is held dissolved or suspended in a polymer matrix, and through which the drug diffuses to the skin. Devices incorporating a reservoir will deliver a steady drug flux across the membrane as long as excess undissolved drug remains in the reservoir; matrix or monolithic devices are typically characterized by a falling drug flux with time, as the matrix layers closer to the skin are depleted of drug. To date limited commercial exploitation of this technology has been achieved, because of the many practical problems to be overcome with real devices. The skin is an effective barrier against the majority of drugs. Unless the delivery device is made unacceptably large, or the natural skin permeation rate of the drug is somehow increased by the use of enhancers, then the drug flux across the skin is inadequate for useful therapy. Thus although in theory any drug might be delivered by this route, serious investigation of candidate drugs has been limited to those few that exhibit suitable properties, namely: small molecular size; short half-life; they are metabolized rapidly by the liver, and thus difficult to administer orally; high in vivo skin permeability; and small effective therapeutic dose. Despite active work in the field since at least 1970, at present commercial patches are available for delivery of only four drugs: nitroglycerin, scopolamine, clonidine, and estradiol.

The U.S. Surgeon General has determined that cigarette smoking is a major risk factor in coronary heart disease and is the cause of approximately 30% of all cancer deaths. However, it is very difficult to give up smoking, and any smoking cessation therapy has to deal with both the pharmacological and the psychological dependence on cigarettes. Separating the treatment of these two factors is an approach that has been tried with modest success, for example by satisfying the pharmacological craving with nicotine pills or chewing gum, while treating the psychological dependence. The difficulty with oral administration is that it leads to irregular and unpredictable blood plasma levels. To date, the best results have been obtained with nicotine chewing gum, which achieves direct delivery to the systemic circulation by buccal absorption. However, chewing gum formulations taste bad, may lead to mouth ulcers and heartburn, cannot be used effectively by denture wearers, and dosage control depends too much on patient compliance.

The concept of applying the teachings of transdermal drug therapy to the delivery of nicotine, which is not a therapeutic drug, is described in U.S. Pat. No. 4,597,961. This patent discloses a transdermal patch comprising an occlusive backing, a nicotine reservoir containing liquid nicotine, either alone or with a carrier or solvent, and a microporous membrane. Nicotine is highly lipid soluble, so no enhancement of the skin permeation rate is necessary to achieve a blood plasma level comparable with that obtained from smoking. Nicotine is highly toxic, and the addition of oils or gels that may dilute the nicotine in the reservoir, and hence slow the flux through the microporous membrane, is suggested in the above patent. All the controlled release embodiments described in the patent, however, employ a microporous membrane, and there is no suggestion that it would be possible to control the delivery of nicotine at a dose that is large enough to satisfy or alleviate the physiological craving, but that is below the toxic threshold, in some other way. The duration of nicotine delivery from the patch disclosed in U.S. Pat. No. 4,597,961 is of the order 30–45 minutes. To maintain nicotine plasma levels sufficiently high to alleviate the craving for cigarettes, the application of many patches per day would then be necessary.

The present invention is directed to the discovery that in spite of nicotine being very volatile and highly toxic, it is possible to make a simple monolithic device that can contain and release nicotine at useful, yet non-toxic levels, for periods of 24 hours or more.

SUMMARY OF THE INVENTION

It is an object of the present invention then to provide a transdermal patch that can be used in the treatment of patients suffering from nicotine addiction.

It is a further object of the invention that said patch be capable of sustained controlled release of nicotine for an extended period of time.

It is a further object of the invention that said device have a monolithic configuration, that does not require a discrete membrane layer for control of nicotine flux.

Further objects of the invention will be apparent from the description of the invention to those skilled in the art.

The present nicotine dispensing patch comprises an impermeable backing layer, a polyurethane matrix in which liquid nicotine is dispersed, and an adhesive layer that holds the patch in contact with the skin of the wearer. The patch may also include a peel strip that protects the device during storage, and that is removed when the patch is placed on the skin.

The impermeable backing and the peel strip may conveniently be made from the same material. Their nature is not critical to the invention, and a variety of commercially available materials can be used. The material chosen should be impermeable to nicotine, and opaque, because nicotine degrades when exposed to ultraviolet light. The adhesive must meet requirements more stringent than those for a simple "Band Aid". It should not permit excessive migration from the matrix into the adhesive during storage; it should not interact with nicotine; it should adhere firmly to the monolithic matrix, and firmly but removably to the peel strip; it should stick securely to the wearer for extended periods, yet allow the patch to be removed with minimum discomfort; and it should not give rise to skin irritation, allergic reactions or other dermatological problems. Preferably a bioadhesive that has an existing record of use in transdermal devices should be used, for example an acrylic- or silicone-based adhesive or polyisobutylene. Optionally a double-adhesive-coated medical tape may be used. It is envisaged that the adhesive would normally form a continuous layer across the entire surface of the device; however embodiments in which the adhesive is disposed as a ring surrounding the active area of the patch are also possible.

The nicotine-loaded matrix is prepared by dissolving a polyether-type polyurethane in an appropriate solvent, adding liquid nicotine and homogenizing the mixture. The matrix mixture is then cast onto the backing material by any of the techniques for polymer casting known in the art. After curing, a thin adhesive film is cast onto the matrix, or double-sided medical adhesive tape is attached. The adhesive is covered by the release liner, and patches of the desired size cut out by punching. The finished patches may be heat sealed into foil pouches, and stored until needed.

The patches of the present invention are preferably designed to replace one day's intake of nicotine from cigarettes. The amount of nicotine released by the patch during use will be approximately in the range 5 mg to 25 mg, corresponding to a consumption of between 5 and 25 cigarettes per day. The size of the patch will depend on the amount of nicotine to be dispensed, but will typically be in the range 2 cm$^2$ to 20 cm$^2$.

DETAILED DESCRIPTION OF THE INVENTION

Figure 1:
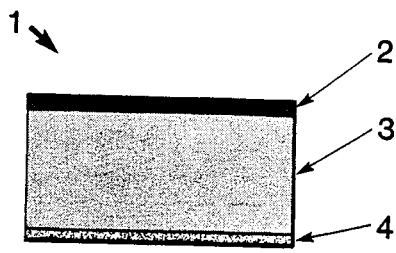
FIG. 1 shows a basic embodiment of the invention including an impermeable backing, a nicotine-containing matrix, and an adhesive layer.

Referring now to FIG. 1, the figure shows a schematic representation of a preferred embodiment of the invention. The transdermal patch 1, comprises an impermeable backing layer 2, a nicotine loaded matrix 3, and an adhesive layer 4.

The impermeable backing layer 2 defines the top of the patch, in other words the side furthest away from the skin in use. The functions of the backing layer are to prevent evaporation of nicotine from the patch, and to protect the patch. The material chosen for the backing layer should be impermeable to nicotine, and opaque to ultraviolet light. Ideally, the backing material should be capable of forming a support onto which the nicotine-containing matrix can be cast, and to which it will bond securely when cast. The backing layer may be made from standard commercially available films for medical use, such as those supplied by 3M Corporation, Dow Chemical, or Fasson Medical Industries. Typically such films are made from polyester or the like, and may be pigmented or metallized. A preferred backing layer is, for example, Scotchpak ® 1005 or 1109, skin-colored, aluminized polyester tapes obtainable from 3M Company, St. Paul, Minn. As an alternative to casting the matrix directly on the backing, the polymer matrix may be cast separately and later stuck to the backing layer.

The nicotine matrix layer 3 comprises liquid nicotine dispersed in a polyurethane matrix. Polyether-type polyurethanes are preferred, because in general they are more inert than polyester-types, and thus more appropriate for biomedical use. Polyether-type polyurethanes are typically made by reacting a hydroxyl-terminated polyether oligomer with a diisocyanate according to the reaction:

where R is a polyether group. This prepolymer is then further reacted with another diol where R is small, for example, 1,4-butanediol, to yield a thermoplastic, rubbery polymer, the properties of which can be tailored by adjusting the proportions of polyether and butane diols. Polymers of this type are available commercially in grades approved for medical use from Dow Chemical, Midland, Mich., under the name Pellethane ® 2363. Different hardnesses are available; the softer grades are generally preferred in the context of the present invention, because they are easier to dissolve.

The adhesive layer 4 should satisfy the general criteria for adhesives for transdermal devices described in the summary section above. In addition it should present a resistance to nicotine permeation that is small compared with the resistance of the polymer matrix layer. Suitable adhesives for use in the practice of the invention include pressure-sensitive adhesives approved for medical use. An amine-resistant adhesive is preferred, so that the adhesive will not be attacked by the nicotine. A range of silicone-based amine-resistant medical adhesives is offered by Dow Chemical. In the context of the present invention, grade BIO PSA Q7-2920, or similar grades are the preferred choice. Alternatively a polyisobutylene-type adhesive may be used.

Optionally, the invention may include a peel strip or release liner. This covers the surface of the pressure-sensitive adhesive during storage, and prevents evaporative loss of nicotine that may have migrated into the adhesive layer. The peel strip may be made from any impermeable film such as is specified for the backing layer. Additionally it may be made from metal foil, Mylar or any material normally used for this purpose in the art that is compatible with nicotine and the chosen adhesive. It is frequently convenient to use the same material as is used for the backing layer. Thus 3M Scotchpak films 1005 or 1109, as described above, are a preferred choice.

Figure 2:
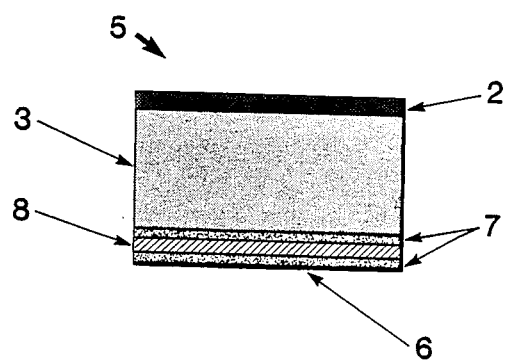
FIG. 2 shows an alternative embodiment where the adhesive layer comprises a double-sided medical adhesive tape.

Referring now to FIG. 2, an alternative embodiment, 5, is shown, comprising a backing layer 2, a matrix layer 3, and an adhesive layer 6. The backing and matrix layers are as described for FIG. 1, but the adhesive layer 6 is now formed from a double-sided medical adhesive tape, having adhesive surfaces 7, and tape layer 8, such as 3M-1778, available from 3M Company. In this case, the medical tape may operate simply as an adhesive, such that the resistance of this layer to nicotine permeation is less than that of the matrix material, as in the embodiment of FIG. 1. On the other hand, if the tape contains a polymer backbone such as polyethylene, which is relatively impermeable to nicotine, then the adhesive layer may be less permeable to nicotine than the matrix material, so that the adhesive layer then serves as a thin membrane limiting flux of nicotine from the device. In embodiments where it is desirable or necessary to load the matrix with a high percentage of nicotine, say 30wt % or above, it may be preferable to use such a rate-controlling tape. The system then functions as a mixed monolithic/reservoir system, where the release characteristics depend both on the matrix polymer and the adhesive backbone polymer. The initial high nicotine flux from the device is then reduced by the presence of the tape to keep it within therapeutically acceptable levels. The nicotine flux through the tape should preferably be of the same order as the flux from the matrix, and would typically be in the range 25–300 $\mu g/cm^2 \cdot h$.

The patch may be assembled by any of the techniques known in the art for laminating transdermal patches. Typically the first step in preparation of the patch is to prepare a solution of the polymer matrix material. Solvents that may be used to dissolve polyurethane include tetrahydrofuran (THF, T425-4 Fischer Scientific, Springfield, N.J.), dimethylchloride (DMC), and dimethylformamide (DMF). Tetrahydrofuran is the preferred solvent, because it has been approved for use with medical materials so long as the residue remaining in the material after curing does not exceed 1.5 wt %. Typically the percentage by weight of polyurethane in the solution will be in the range 5% to 35%, depending on the solvent and the polyurethane grade. Using THF, it is possible to prepare casting solutions with relatively high concentrations, typically around 20 to 25%, of a soft grade polyurethane. The harder grades are more difficult to dissolve. It is usually desirable to make the concentration of polyurethane in the solvent as high as possible. The solution as cast is then closer in thickness to the finished film. Also, concentrated solutions are more viscous, and it has been found that, in general, better embodiment of nicotine in the matrix is achieved from viscous solutions. Liquid nicotine is then added to the polymer solution, and the mixture is homogenized. The percentage by weight of nicotine in the solution may be varied according to the desired loading of the finished matrix. The nicotine content of the finished matrix may vary widely, from around 5 wt % up to about 50 wt %. Above about 50 wt % nicotine, the matrix is attacked by the nicotine. Matrices containing a nicotine loading of around 30 wt % or above may, at least initially, release nicotine too rapidly for optimum therapy. This initial high release may be reduced by using a double-sided adhesive tape with a polyethylene or similar backbone, which presents an additional resistance to nicotine permeation. The release characteristics of the combined system may then be appropriate for some dosage levels. Where it is desired to release between 5 mg and 20 mg of nicotine in a 24-hour period, the preferred nicotine loading in the matrix is 10 wt % to 20 wt %. Nicotine is very volatile, and according to the way in which the curing is done, the matrix may lose up to 30% of its nicotine content through evaporation. Therefore it is desirable to start with a nicotine content in the mixture that is substantially higher than the required finished loading. The matrix material may be poured into a mold or cast alone or on the desired backing material. The casting should then be covered, and left to cure slowly at room temperature. After curing, the matrix will typically have a thickness in the range 50 to 800 microns. It will be appreciated that for a given total nicotine load, the percentage loading may be varied by varying the matrix thickness. In embodiments where the matrix is formed apart from the backing layer, a backing may be provided by attaching a layer of single-sided occlusive medical adhesive tape to one face of the matrix. A thin film of adhesive is then cast on the face of the matrix away from the backing. Optionally a double-sided medical adhesive tape may be substituted for the cast adhesive. A typical double-sided tape that may be used is 3M-1778, a microporous tape available from 3M Company. To prevent evaporation of nicotine that diffuses into the adhesive layer during storage, it is preferable to cover the adhesive layer with a peel strip as described above. Patches of he desired size may then be punched out from the laminate. The size of the patch will vary according to the amount of nicotine that is to be dispensed. It is envisaged that the patches would be worn for periods up to at least 24 hours, during which time the amount of nicotine delivered would be in the range 5 mg to 25 mg, equivalent to the daily nicotine intake of very light to moderately heavy smokers. Skin permeability to nicotine is of the order of 100 $\mu g/cm^2 \cdot h$, so to deliver 5 mg in 24 hours, a patch approximately 2 $cm^2$ in area is needed. Likewise to deliver 25 mg the patch size should be around 10 $cm^2$.

Prior to use, the patches should be stored in foil pouches, both to prevent contamination and to avoid nicotine loss. Such pouches are standard in the industry, and are available from, for example, Lithotype Co., San Francisco, Calif.

The invention is now further illustrated by Examples 1-5, which are exemplary but non-limiting.

EXAMPLE 1

Figure 3:
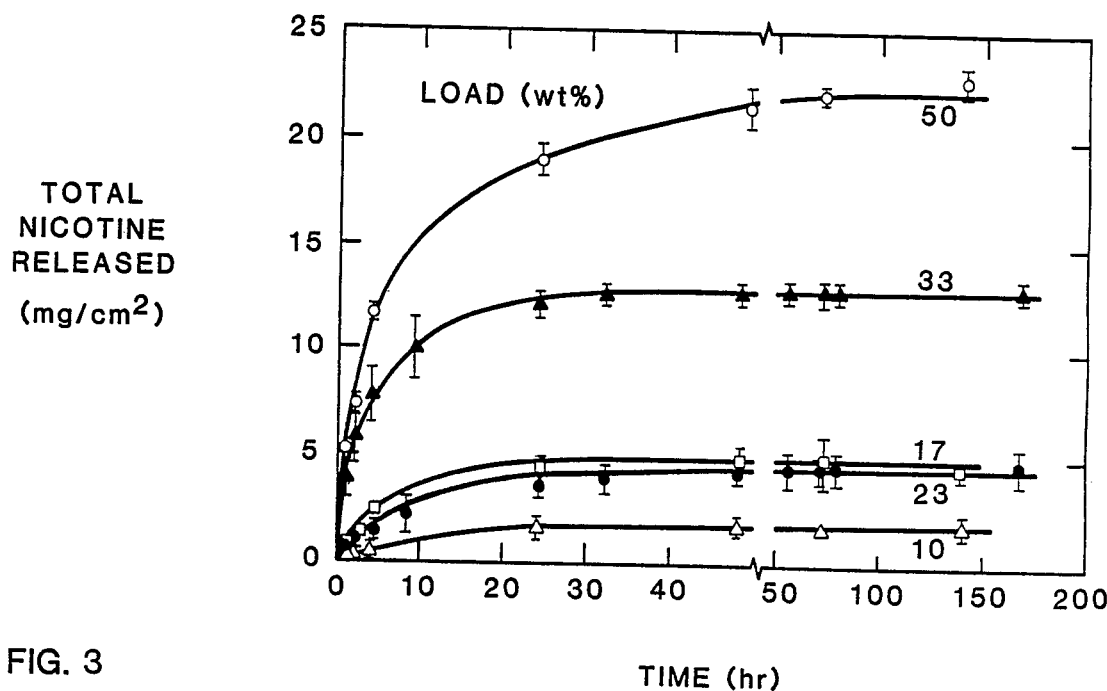
FIG. 3 is a graph of total nicotine released from polyurethane matrices loaded with 10 wt % to 50 wt % nicotine.

Monolithic patches were made as follows. A solution of nicotine-loaded Pellethane 2363-80AE was made by mixing Pellethane pellets into tetrahydrofuran, adding 10 wt % liquid nicotine, and agitating on a bottle roller for three days. A layer of backing material grade 3M-1005 was spread in a petri dish and covered with the matrix mixture. The petri dish was covered, and the matrix was left to cure for 10 days at room temperature. Patches with an area of 3.88 $cm^2$ were cut from the finished matrix with a punch, and device release-rate measurements were made as follows. Each test device was suspended in a wire cage in an isotonic saline solution, constantly agitated by a magnetic stirrer, and maintained at 30° C. Periodic saline samples were taken for HPLC analysis using a Novapak ® C18 column. The results are given by the lowest curve in FIG. 3.

EXAMPLE 2

Monolithic patches were made and tested by the same procedure as described in Example 1, except that the nicotine content of the matrix mixture was 17 wt %. The results of the release tests are given by the second curve in FIG. 3.

EXAMPLE 3

Monolithic patches were made and tested by the same procedure as described in Example 1, except that the nicotine content of the matrix mixture was 23 wt %. The results of the release tests are given by the third curve in FIG. 3.

EXAMPLE 4

Monolithic patches were made and tested by the same procedure as described in Example 1, except that the nicotine content of the matrix mixture was 33 wt %. The results of the release tests are given by the fourth curve in FIG. 3.

EXAMPLE 5

Monolithic patches were made and tested by the same procedure as described in Example 1, except that the nicotine content of the matrix mixture was 50 wt %. The results of the release tests are given by the fifth curve in FIG. 3.

We claim:

1. A transdermal nicotine delivery device, comprising a laminate of:
   (a) a matrix layer comprising between about 5% and 50% nicotine and between about 95% and 50% polyurethane, said matrix layer having a first and second face;
   (b) an impermeable and opaque backing layer contacting said first face; and
   (c) an amine-resistant bioadhesive layer contacting said second face.

2. A transdermal nicotine delivery device, comprising a laminate of:
   (a) a matrix layer comprising between about 5% and 50% nicotine and between about 95% and 50% polyester-type polyurethane, said matrix layer having a first and second face;
   (b) an impermeable and opaque backing layer contacting said first face; and
   (c) an amine-resistant bioadhesive layer contacting said second face.

3. The transdermal device of claim 1 or claim 2, wherein said matrix layer comprises between about 5% and 25% nicotine and between about 95% and 75% polyurethane.

4. The transdermal device of claim 1 or claim 2, wherein said amine-resistant bioadhesive layer comprises double-sided medical adhesive tape.

5. The transdermal device of claim 1 or claim 2, wherein said amine-resistant bioadhesive layer has a nicotine flux between 25 and 300 $\mu g/cm^2 \cdot h$.

6. A method for prolonged transdermal delivery of nicotine to a patient, comprising applying to said patient a transdermal nicotine delivery device, comprising a laminate of:
   (a) a matrix layer comprising between about 5% and 50% nicotine and between about 95% and 50% polyether-type polyurethane, said matrix layer having a first and second face;
   (b) am impermeable and opaque backing layer contacting said first face; and
   (c) an amine-resistant bioadhesive layer contacting said second face.

7. A method for prolonged transdermal delivery of nicotine to a patient, comprising applying to said patient a transdermal nicotine delivery device, comprising a laminate of:
   (a) a matrix layer comprising between about 5% and 50% nicotine and between about 95% and 50% polyether-type polyurethane, said matrix layer having a first and second face;
   (b) an impermeable and opaque backing layer contacting said first face,
   (c) an amine-resistant bioadhesive layer contacting said second face, said transdermal nicotine device remaining active on the skin for a period of one day.

* * * * *